United States Patent [19]

Freerks et al.

[11] 3,977,998

[45] Aug. 31, 1976

[54] PROCESS FOR PREPARING PHOSPHORUS-VANADIUM-OXYGEN CATALYSTS

[75] Inventors: Marshall C. Freerks, Kirkwood; Ramon A. Mount, St. Louis, both of Mo.

[73] Assignee: Monsanto Company, St. Louis, Mo.

[22] Filed: Sept. 3, 1974

[21] Appl. No.: 502,475

[52] U.S. Cl................................ 252/435; 252/437; 260/346.8 A
[51] Int. Cl.²......................................... B01J 27/18
[58] Field of Search........................... 252/435, 437; 260/346.8 A

[56] References Cited
UNITED STATES PATENTS

| | | | |
|---|---|---|---|
| 3,293,268 | 12/1966 | Bergman et al. | 260/346.8 A |
| 3,864,280 | 2/1975 | Schneider | 252/437 X |

*Primary Examiner*—W. J. Shine
*Attorney, Agent, or Firm*—Neal E. Willis; John E. Maurer; Frank D. Shearin

[57] ABSTRACT

The performance of phosphorus-vanadium-oxygen catalysts useful for the conversion of saturated aliphatic hydrocarbons to maleic anhydride is dependent on the controlled calcination of the catalyst precursor. Phosphorus-vanadium-oxygen catalysts are prepared by mixing phosphorus and vanadium compounds to form precursors containing tetravalent vanadium, and calcining the precursors in an oxidizing atmosphere until a controlled level of pentavalent vanadium has been achieved, and then calcining the precursors in an inert atmosphere to higher temperatures to provide catalysts with the desired oxidation levels that are promptly active, so that valuable manufacturing facilities are not required to "activate the catalyst."

5 Claims, No Drawings

PROCESS FOR PREPARING PHOSPHORUS-VANADIUM-OXYGEN CATALYSTS

BACKGROUND OF THE INVENTION

This invention relates to a method for preparing catalysts useful in the manufacture of dicarboxylic acid anhydrides by the oxidation of hydrocarbons. More particularly, it is directed to the preparation of catalysts suitable for producing maleic anhydride from saturated hydrocarbons.

Maleic anhydride is of significant commercial interest throughout the world. It is used alone or in combination with other acids in the manufacture of alkyd and polyester resins. It is also a versatile intermediate for chemical synthesis. Significant quantities of maleic anhydride are produced each year to satisfy these needs.

The prior art discloses a number of catalysts used in the conversion of organic feed stocks to maleic anhydride. As an example, U.S. Pat. No. 2,773,836 discloses phosphorus-vanadium-oxygen catalysts for the conversion of olefins to maleic anhydride. The catalysts had a weight ratio of $V_2O_5$ to $P_2O_5$ of 3:2 to 1:2, and were prepared by adding a vanadium compound to phosphoric acid, optionally adding a carrier to the solution, removing the excess liquid by evaporation, drying the remaining material at 200°–400°F., grinding the resulting solids, and heating to 700°–1100°F. for several hours. U.S. Pat. No. 3,156,707 also discloses a similar method for preparing phosphorus-vanadium-oxygen catalysts for the conversion of olefins to maleic anhydride. The vanadium in these catalysts was reduced to an average valence in the range of 2.5 to 4.6 using an acid such as hydrochloric acid or oxalic acid during the preparatory steps, but the materials were calcined at elevated temperatures in air before use as catalysts.

Of particular interest is U.S. Pat. No. 3,293,268 which teaches a process of oxidizing saturated aliphatic hydrocarbons to maleic anhydride under controlled temperature conditions and in the presence of phosphorus-vanadium-oxygen catalysts. One method taught in that patent for preparing catalysts comprised reacting phosphoric acid with a vanadium compound in aqueous hydrochloric acid solution, recovering the remaining solids containing tetravalent vanadium by evaporating the solution to dryness, and then heating the solids to about 450°C. for two hours. The solids were ground to pass a 20 mesh screen and pelleted to form tablets. The tablets were then charged to a fixed catalyst bed in a test reactor at room temperature and the reactor heated for 16 hours at 400°C. Thereafter, a 0.5 volume percent butane in air mixture was passed through the catalyst in a fixed tube reactor at temperatures above 400°C. to form maleic anhydride before the catalyst was used in successive runs to convert butane to maleic anhydride.

All of these teachings in the prior art fail in one or more ways to achieve the results obtained by the use of the present invention. When phosphorus-vanadium-oxygen catalysts as prepared by the prior art, are calcined at elevated temperatures, the vanadium is oxidized to the pentavalent state. If the calcination is not conducted at too high a temperature, or over too long a period of time, the catalysts can be conditioned by passing a saturated hydrocarbon in air mixture over the catalysts at elevated temperatures to reduce the vanadium before the saturated hydrocarbon is converted to maleic anhydride in high yields. Sometimes, calcination at elevated temperatures over too long a time converts the vanadium to the pentavalent state, and the catalyst is not suitable for the conversion of saturated hydrocarbons to maleic anhydride. On the other hand, the present invention provides the art with a process of calcining a phosphorus-vanadium-oxygen catalyst to carefully control the level of vanadium in the pentavalent state. Thus, the catalysts prepared by the process of the present invention can be used for the conversion of saturated hydrocarbons to maleic anhydride without an activation step that requires the use of valuable production facilities for calcination or activation, rather than for the conversion of saturated hydrocarbons to maleic anhydride.

SUMMARY OF THE INVENTION

It is an object of this invention to provide a process for preparing improved phosphorus-vanadium-oxygen catalysts suitable for converting saturated hydrocarbons to maleic anhydride. It is another object to provide improved phosphorus-vanadium-oxygen catalysts particularly suitable for converting butane to maleic anhydride.

These and other objects are achieved by the process disclosed herein for preparing phosphorus-vanadium-oxygen catalysts having a phosphorus to vanadium atom ratio in the range of about 1:2 to about 2:1, comprising the steps of:

a. contacting vanadium compounds and phosphorus compounds under conditions which will provide at least 50 atom percent of the vanadium in the tetravalent state to form a catalyst precursor;
b. recovering the catalyst precursor; and
c. calcining the catalyst precursor at temperatures from about 350°C. to about 600°C. for at least two hours in an inert atmosphere.

For the purposes of this invention, the term "catalytic activity" means the ability to convert a particular feed stock, such as butane, at a particular temperature to other compounds. The term "selectivity" means the ratio of the moles of maleic anhydride obtained to the moles of hydrocarbon reacted. The term "yield" means the ratio of the moles of maleic anhydride obtained to the moles of feed introduced into the reaction. The term "space velocity" means the hourly volume of gaseous feed expressed in cubic centimeters (cc) at 60°F. and standard atmospheric pressure, divided by the catalyst bulk volume expressed in cubic centimeters (cc), the term expressed as cc/cc/hour.

The catalysts of this invention are particularly useful for the conversion of butane to maleic anhydride. These catalysts have characteristics which distinguish them from prior art catalysts used in the manufacture of dicarboxylic acid anhydrides, and the methods by which the present catalysts are prepared caused these distinguishing characteristics. Details of the catalyst preparation, their distinguishing characteristics and means by which such characteristics can be determined and the use of the present catalysts to convert saturated hydrocarbons to maleic anhydride are hereinafter described.

Broadly described, the catalysts of this invention are prepared by contacting vanadium and phosphorus compounds under conditions which will provide a substantial amount of vanadium in the tetravalent state to form catalyst precursors, recovering the catalyst precursors, and calcining the catalyst precursors to form the catalyst.

The vanadium compounds useful as a source of vanadium in the catalyst precursors are those known to the art. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as metavanadic acid, pyrovanadic acid and the like; vanadium salts such as ammonium metavanadate, vanadium sulfate, vanadium phosphate, vanadyl formate, vanadyl oxalate and the like. However, vanadium pentoxide is preferred.

As a source of phosphorus in the catalyst precursors useful phosphorus compounds are also those known to the art. Suitable phosphorus compounds include: phosphoric acids, such as metaphosphoric acid, orthophosphoric acid, triphosphoric acid, pyrophosphoric acid, phosphorous acid and the like; phosphorus oxides such as phosphorus pentoxide and the like; phosphorus halides such as phosphorus oxyiodide, phosphorus pentachloride, phosphorus oxybromide and the like; and organophosphorus compounds such as ethyl phosphate, methyl phosphate and the like. However, a mixture of phosphoric acid and phosphorous acid is preferred.

To prepare the catalyst precursors, a vanadium compound is heated with a phosphorus compound in an acid solution to dissolve the starting materials. A reducing agent is used to reduce any pentavalent vanadium to tetravalent vanadium and to maintain vanadium in the tetravalent state. As is well known to those skilled in the art, hydrogen halide acid or oxalic acid solutions, which are mild reducing agents, can serve not only as the acid but also as the reducing agent for the pentavalent vanadium. On the other hand, phosphoric acid containing sufficient phosphorus acid to reduce the pentavalent vanadium can serve as the acid, as the reducing agent and as a source of phosphorus for the catalyst precursors, and this mixture of phosphoric acid and phosphorous acid is preferred. The acid solution containing phosphorus compounds and vanadium compounds are heated until a blue solution is obtained, indicating that a substantial amount, i.e. greater than 50 atom percent, of the vanadium is in the tetravalent state. The amount of time required to dissolve the phosphorus and vanadium compounds and to reduce a substantial amount of the vanadium to the tetravalent state to form the catalyst precursors varies from batch to batch, depending upon the compounds used as starting materials and the temperature at which the compounds are heated. However, as will occur to those skilled in the art, an aliquot of the solution can be analyzed to insure that most of the vanadium is in the tetravalent state.

Although any number of phosphorus compounds and vanadium compounds can be used to form the phosphorus-vanadium-oxygen precursor, the atom ratio of phosphorus to vanadium in the precursor is important since it controls the phosphorus to vanadium atom ratio in the final catalyst. When phosphorus-vanadium-oxygen precursors contain a phosphorus to vanadium atom ratio below about 1:2 or above about 2:1, the yield of maleic anhydride using the catalysts of this invention is so low that it is not of commercial significance. It is preferred that phosphorus-vanadium-oxygen precursors have a phosphorus to vanadium atom ratio in the range of about 1:1 to about 1.5:1, and more preferably to have a phosphorus to vanadium atom ratio of about 1:1 to about 1.2:1, say about 1.1:1.

After the vanadium and phosphorus compounds are mixed and substantially all the vanadium has been reduced to the tetravalent state, it is necessary to recover the phosphorus-vanadium-oxygen precursors. Techniques for recovering the phosphorus-vanadium-oxygen precursors from solution and techniques for forming the precursors for use in a fluidized bed reactor or in a fixed tube heat exchanger type reactor are well known to those skilled in the art. As an example, the precursors can be dried by gentle heating to recover the solid phosphorus-vanadium-oxygen precursors from solution. The precursors can be recovered by depositing the phosphorus-vanadium-oxygen precursors from solution on a carrier such as titania or alumina. Alternatively, the dried precursors can be comminuted for use in a fluidized bed reactor, or the precursors can be prepared for use in a fixed tube reactor by prilling or tabletting the precursors.

In a preferred embodiment, the aqueous solution containing the phosphorus-vanadium-oxygen precursor is evaporated to apparent dryness. Then, from about 10 to about 40 weight percent water is added to the precursor to form a putty. Alternatively, only so much of the water from the aqueous solution of phosphorus-vanadium-oxygen precursor is removed as is necessary to form a viscous putty. The amount of water in the putty is not critical provided that there is sufficient water to permit forming into a suitable structure as by extrusion or pelleting, but not so much water as to cause the wet mixture to slump after it is formed. A putty containing less than about 10 weight percent water is difficult to extrude whereas a putty containing greater than about 40 weight percent water will normally slump and not hold its shape. However, it should be noted that various additives, such as a gelling agent or a lubricant, can be added to the putty that can change this ratio, as will occur to those skilled in the art. The putty of precursor and water is then structured by extruding the putty through a die, drying the extrudate and dividing the extrudate into pellets or tablets. Alternatively, the extrudate can be divided into pellets before drying and this latter procedure is preferred.

After the precursors have been recovered as described above, it is critical in the process of the present invention to calcine the phosphorus-vanadium-oxygen precursors in an oxygen containing gas until about 20 to about 95 atom percent of the vanadium is in the pentavalent state and then calcining the precursor in an inert atmosphere, such as nitrogen or a noble gas, i.e. helium, argon, neon, krypton, xenon, at temperatures of about 350°C. to about 600°C. for at least about two hours to convert the precursors to the catalysts of the present invention. The reason for the beneficial effect of using an inert atmosphere is not understood at this time although it is believed that the inert atmosphere prevents excessive oxidation of the tetravalent vanadium to pentavalent vanadium as the precursor is calcined. It is preferred to calcine the precursors in air at temperatures of about 350°C. to about 600°C. until about 20 to about 95 atom percent of the vanadium has been oxidized to pentavalent vanadium. If more than about 95 atom percent of the vanadium is oxidized to pentavalent vanadium, usually caused by calcining too long or at too high a temperature, the selectivity of the catalysts and the yield of maleic anhydride decrease markedly. On the other hand, oxidation of less than about 20 atom percent of the vanadium during air calcination does not seem to be more beneficial than calcination in an inert atmosphere. It is more preferred to calcine the precursor in air until about 40 atom percent to about 80 atom percent of the vanadium has been oxidized to pentavalent vanadium, and thereafter calcining at 350°C. to 600°C. in an inert atmosphere.

After the phosphorus-vanadium-oxygen precursors have been calcined to form the phosphorus-vanadium-oxygen catalysts of this invention, the catalysts can be used to convert a saturated hydrocarbon to maleic anhydride. However, the initial yield of maleic anhydride may be low, and if this is the case, the catalysts can be "conditioned" as will occur to those skilled in the art, by passing low concentrations of saturated hydrocarbons in air at slow space velocities through the catalysts for a period of time before production operations begin.

The catalysts of the present invention are useful in a variety of reactors to convert saturated hydrocarbons to maleic anhydride. Both fluidized bed reactors and fixed tube heat exchanger type reactors are satisfactory, and the details of the operation of such reactors are well known to those skilled in the art. The reaction to convert saturated hydrocarbons to maleic anhydride requires only passing the saturated hydrocarbons admixed with a free oxygen-containing gas, such as air or oxygen enriched air, through the catalysts at elevated temperatures. The saturated hydrocarbons are passed through the catalysts at a concentration of about 1.5 to about 10 volume percent saturated hydrocarbons at a space velocity of about 100 to 4000 cc/cc/hour to provide maleic anhydride yields of greater than 40 percent at temperatures between about 350°C. and 600°C.

In the preferred embodiment the catalysts of the present invention are particularly useful in fixed tube heat exchanger type reactors. The tubes of such reactors can vary in diameter from about ¼ inch to about 1.5 inch and the length can vary from about 6 inches to about 10 or more feet. It is desirable to have the surfaces of the reactors at a relatively constant temperature and some medium to conduct heat from the reactors is necessary to aid temperature control. Such media can be Wood's metals, molten sulfur, mercury, molten lead and the like, or eutectic salt baths. A metal block reactor whereby the metal surrounding the tube acts as a temperature regulating body can also be used. The reactor or reaction tubes can be iron, stainless steel, carbon steel, glass and the like.

Maleic anhydride produced by using the catalysts of this invention can be recovered by any number of means well known to those skilled in the art. For example, the maleic anhydride can be recovered by direct condensation or by absorption in suitable media with subsequent separation and purification of the anhydride.

The pressure in the reactor is not generally critical; therefore, the reaction can be atmospheric, superatmospheric and subatmospheric pressure, although superatmospheric pressure is usually employed.

A large number of saturated hydrocarbons having from 4 to 10 carbon atoms can be converted to maleic anhydride using the catalysts of the present invention. It is only necessary that the hydrocarbon contains not less than four carbon atoms in a straight chain. As an example, the preferred saturated hydrocarbon is butane, but isobutane, which does not contain four carbon atoms in a straight-chain, is not satisfactory for conversion to maleic anhydride although its presence is not harmful. In addition to butane, other saturated hydrocarbons within the scope of this invention include the pentanes, the hexanes, the heptanes, the octanes, the nonanes, the decanes or mixtures of any of these with or without butane. In addition to the above compounds, cyclic compounds such as cyclopentane or cyclohexane are satisfactory feed materials for conversion to maleic anhydride. Also, the feed stocks do not necessarily have to be totally saturated but can be technical grade hydrocarbons containing up to about 25 weight percent of olefinically unsaturated hydrocarbons, or other hydrocarbon fractions.

The principle product from the oxidation of the above feed materials is maleic anhydride. It should be noted that small amounts of citraconic anhydride may also be produced when the feed stock is a saturated hydrocarbon containing more than 4 carbon atoms.

DESCRIPTION OF THE PREFERRED EMBODIMENTS

This invention is further illustrated by, but not limited to, the following examples:

EXAMPLE I

A phosphorus-vanadium-oxygen catalyst was prepared by slowly adding 133.08 grams of vanadium pentoxide to a mixture of 450 milliliters of water, 50.6 grams of 85% phosphoric acid and 91.7 grams of 99.4% phosphorus acid. The phosphorus to vanadium atom ratio was about 1.05:1. The mixture of vanadium and phosphorus compounds was placed in an autoclave, which was heated to about 100°C. and thereafter sealed. The autoclave containing the vanadium and phosphorus compounds was heated to about 145°C. for about three hours. After the autoclave was cooled and opened, a phosphorus-vanadium-oxygen precursor was observed in a water suspension. The precursor was recovered from the water and mixed with about 20 weight percent water, based on the dry weight of the precursor, to form a viscous putty, which was then extruded through a 0.35 cm diameter die. The extrudate was cut into pellets of about 0.35 cm lengths, allowed to air-dry, and then heated to about 125°C.

The precursor pellets were then charged to a muffle furnace, and the furnace was heated to about 350°C. over a one-hour period. During the next hour the temperature of the furnace was increased to 375°C. Thereafter, the air in the muffle furnace was replaced with nitrogen, and the temperature of the furnace increased to 500°C. over a five-hour period. The heating was then discontinued, and the resulting catalyst was rapidly cooled to room temperature under nitrogen. Analysis of a sample of the catalyst revealed that about 93 atom % of the vanadium was in the tetravalent state.

About 50 cc of the catalyst pellets were then charged to a 2.54-cm outside diameter fixed-bed, glass reactor, which gives results comparable to those obtained in a production reactor. After 12 hours at a space velocity of about 1500 cc/cc/hour using a butane in air mixture of about 1.5 mole % butane and at a temperature of about 465°C. the yield of maleic anhydride was about 34 mole %.

EXAMPLE II

The procedure of Example I was repeated except that the precursor pellets in the muffle furnace were heated to about 350°C. in one hour, and heated to about 400°C. in the next two hours. Thereafter, the air in the muffle furnace was replaced with nitrogen, and the temperature of the furnace increased to 500°C. over the next four-hour period. Analysis of a sample of the resulting catalyst revealed that about 66 atom % of the vanadium was in the tetravalent state.

When about 50 cc of the catalyst was charged to the maleic anhydride reactor, after 13 hours at about the same conditions used in Example I, the yield of maleic anhydride was about 41 mole %.

Although the invention has been described in terms of specified embodiments which are set forth in considerable detail, it should be understood that this is by way of illustration only and that the invention is not necessarily limited thereto since alternative embodiments and operating techniques will become apparent to those skilled in the art in view of the disclosure. As an example, the phosphorus-vanadium-oxygen catalysts of the present invention can be modified with elements such as titanium, zirconium, zinc, lithium, sodium, potassium, calcium, barium, magnesium and the like, to provide catalysts of improved yields using the process of the present invention. Accordingly, modifications are contemplated which can be made without departing from the spirit of the described invention.

What is claimed is:

1. In a process for preparing a phosphorus-vanadium-oxygen complex catalyst having a phosphorus to vanadium atom ratio in the range of about 1:2 to about 2:1, prepared by:
   a. contacting a vanadium compound and a phosphorus compound in an acid solution containing a reducing agent under conditions which will provide at least 50 atom percent of the vanadium in the tetravalent state to form a catalyst precursor, said vanadium compound and said phosphorus compound being oxides or compounds thermally convertible to the phosphorus-vanadium-oxygen complex catalyst;
   b. recovering the catalyst precursor; and
   c. calcining the catalyst precursor structures at temperatures from about 350°C. to about 600°C. for at least two hours, the improvement which comprises calcining the catalyst precursor structures in an inert atmosphere.

2. In a process of claim 1 wherein the inert atmosphere is nitrogen.

3. In a process of claim 1 wherein the catalyst precursor structures are calcined in an oxygen-containing gas until about 20 to about 95 atom percent of the vanadium is in the pentavalent state, and then calcining the precursor in an inert atmosphere at temperatures of about 350°C. to about 600°C.

4. In a process of claim 3 wherein the catalyst precursor structures are calcined in an oxygen-containing gas until about 40 to about 80 atom percent of the vanadium is in the pentavalent state.

5. In a process of claim 3 wherein the phosphorus to vanadium atom ratio is in the range of about 1:1 to about 1.5:1.

* * * * *